US012808870B2

(12) United States Patent
Arroyo et al.

(10) Patent No.: US 12,808,870 B2
(45) Date of Patent: Nov. 24, 2026

(54) METHODS AND RELATED ASPECTS FOR PATHOGEN DETECTION

(71) Applicant: THE JOHNS HOPKINS UNIVERSITY, Baltimore, MD (US)

(72) Inventors: Netzahualcoyotl Arroyo, Baltimore, MD (US); Jamie Spangler, Baltimore, MD (US); Taekjip Ha, Baltimore, MD (US); Elissa Kathleen Leonard, Baltimore, MD (US); Miguel Aller Pellitero, Baltimore, MD (US); Soojung Claire Hur, Baltimore, MD (US); Harrison Khoo, Cerritos, CA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 803 days.

(21) Appl. No.: 18/044,923

(22) PCT Filed: Sep. 13, 2021

(86) PCT No.: PCT/US2021/050056
§ 371 (c)(1),
(2) Date: Mar. 10, 2023

(87) PCT Pub. No.: WO2022/056373
PCT Pub. Date: Mar. 17, 2022

(65) Prior Publication Data

US 2023/0341396 A1 Oct. 26, 2023

Related U.S. Application Data

(60) Provisional application No. 63/078,130, filed on Sep. 14, 2020.

(51) Int. Cl.
*G01N 33/53* (2006.01)
*B01L 3/00* (2006.01)
(Continued)

(52) U.S. Cl.
CPC .. *G01N 33/56983* (2013.01); *B01L 3/502761* (2013.01); *G01N 33/54386* (2013.01);
(Continued)

(58) Field of Classification Search
None
See application file for complete search history.

(56) References Cited

U.S. PATENT DOCUMENTS 10,822,379 B1 * 11/2020 Dimitrov ............. C07K 14/005
2009/0325276 A1 12/2009 Battrell et al.

FOREIGN PATENT DOCUMENTS

CN 111366525 A * 7/2020 ............. G01N 15/14
WO 2016077738 A1 5/2016
WO WO-2021262728 A1 * 12/2021 ............... C12Q 1/70

OTHER PUBLICATIONS

WIPO English translation of CN111366525A (Year: 2020).*
(Continued)

*Primary Examiner* — M Franco G Salvoza
(74) *Attorney, Agent, or Firm* — MH2 Technology Law Group LLP

(57) ABSTRACT

Provided herein are methods of detecting pathogen antibodies, such as a severe acute respiratory syndrome coronavirus-2 (SARS-CoV-2), in samples. Related devices, kits, reaction mixtures, and systems are also provided.

3 Claims, 10 Drawing Sheets

(51) Int. Cl.
*G01N 33/543* (2006.01)
*G01N 33/569* (2006.01)

(52) U.S. Cl.
CPC .................. *B01L 2200/0647* (2013.01); *B01L 2300/0636* (2013.01); *B01L 2300/0867* (2013.01); *B01L 2300/0883* (2013.01); *B01L 2400/084* (2013.01); *G01N 2333/165* (2013.01); *G01N 2333/928* (2013.01); *G01N 2333/948* (2013.01); *G01N 2469/20* (2013.01)

(56) References Cited

OTHER PUBLICATIONS

Simms, E. (Authorized officer), International Search Report and Written Opinion in corresponding International Application No. PCT/US2021/050056 mailed on Sep. 27, 2021, 15 pages.
Freeman, B. et al. "Validation of a SARS-CoV-2 spike protein ELISA for use in contact investigations and serosurveillance." Biorxiv (2020).
Guo, Tiffany W. et al. "Mobile device for disease diagnosis and data tracking in resource-limited settings." Mobile Health Technologies: Methods and Protocols (2015): 3-14.
Lan, Tian et al. "Detection of protein biomarker using a blood glucose meter." Mobile Health Technologies: Methods and Protocols (2015): 99-109.
Randad, P. R. et al. "COVID-19 serology at population scale: SARS-CoV-2-specific antibody responses in saliva. medRxiv Prepr. Serv." Health Sci 59 (2020).
A, Jhu, "Office of the Provost Funded Research Response to SARS-CoV-2, Adapting Commercial Glucose Sensors to Population-Scale Measurement of SARS-CoV-2 Antibodies", Registration of Research Form Arroyo Lab, (Sep. 19, 2020), (Nov. 23, 2021) [XP] 1-4, 14, 15.
Sabate Del Rio, Jonathan et al. "An antifouling coating that enables affinity-based electrochemical biosensing in complex biological fluids." Nature nanotechnology 14.12 (2019): 1143-1149.
Xiang, Yu et al. "Using personal glucose meters and functional DNA sensors to quantify a variety of analytical targets." Nature chemistry 3.9 (2011): 697-703.
Kobayashi, M. (Authorized officer), International Preliminary Report on Patentability issued in corresponding International Application No. PCT/US2021/050056 mailed on Mar. 23, 2023, 11 pages.

* cited by examiner

METHODS AND RELATED ASPECTS FOR PATHOGEN DETECTION

CROSS-REFERENCE TO RELATED APPLICATIONS

This application is the national stage entry of International Patent Application No. PCT/US2021/050056, filed on Sep. 13, 2021, and published as WO 2022/056373 A1 on Mar. 17, 2022, which claims the benefit of U.S. Provisional Patent Application Ser. No. 63/078,130, filed on Sep. 14, 2020, both of which is are hereby incorporated herein by reference in their entireties.

BACKGROUND

Pandemic pathogens cause severe disease and mortality worldwide. However, there often exists significant uncertainty regarding the extent of asymptomatic and mild cases of the diseases they cause. Furthermore, during early pandemic stages questions often remain regarding the magnitude and duration of antibody response after infection. Thus, gaining a better understanding of herd immunity is important to improving estimates of parameter inputs for "susceptible, infected, and recovered" (SIR) models and for safely resuming economic and social activities globally. One approach for gathering this crucial information is through population-scale, quantitative testing via decentralized, convenient, and non-invasive assays that can be deployed broadly and serially (at scales of hundreds of thousands of tests) to accurately monitor viral infection spread.

The current approach to diagnosing viral infections in many nations focuses on reverse-transcription polymerase chain reaction (RT-PCR) testing of only hospitalized individuals with suspected infection, symptomatic individuals at risk of poor outcomes (e.g., elderly, immunocompromised, etc.), symptomatic persons who had contact with confirmed or suspected cases, and individuals who traveled to affected geographic regions. This approach is necessary to prevent poor outcomes among individuals most likely to suffer disproportionately and not overwhelm the healthcare system. However, there remains a large proportion of community transmission that goes undetected through this tip-of-the-iceberg testing approach. As a consequence, the extent of asymptomatic and mild cases is often poorly understood.

Accordingly, there is a need for additional methods, and related aspects, for a robust, cost-effective biosensing strategy in order to cope with the unprecedented challenge and pathogen detection generally.

SUMMARY

The present disclosure relates, in certain aspects, to methods, devices, kits, reaction mixtures, and systems of use in detecting anti-pathogen antibodies and longitudinally monitoring immunity, including for severe acute respiratory syndrome coronavirus-2 (SARS-CoV-2), in samples. These and other aspects will be apparent upon a complete review of the present disclosure, including the accompanying figures.

In some embodiments, motivated by a need to produce convenient diagnostic platforms for the monitoring of infection spread at population scale, the present disclosure provides a disposable electrochemical diagnostic platform that is autonomous and self-contained, and leverages selected technologies to detect SARS-CoV-2 and other pathogens. In some embodiments, the approach includes three readily deployable elements: (1) a non-invasive oral fluid collector, (2) an autonomous microfluidic device with entry and outlet ports for specimen delivery and analysis; and (3) a glucometer. By using advanced, ultra-soft swabs to painlessly collect oral fluid, certain embodiments of the approaches described herein allow convenient testing in people of all ages. These swabs are supported by a toothbrush-like handle with a connector to be inserted into the entry port of the microfluidic device in some embodiments. In some of these embodiments, the device serially controls the passage of specimen and reagent solutions over an immunoassay pad, which contains enzymes catalyzing the production of glucose proportionally to the number of pathogen (e.g., SARS-CoV-2 or other) antibodies present in the specimen. In some embodiments, the glucose is detected at an outlet port via a glucometer. Such a detection approach is unparalleled and enables serial monitoring of antibody titers in individuals, empowering scientists and clinicians with rapid, quantitative information regarding immunity. Moreover, the convenient design of each element allows large-scale manufacturing and, thus, readily enables infection monitoring at the population scale.

In one aspect, the present disclosure provides a method of detecting an antibody to a pathogen in a sample. The method includes contacting the sample with an epitope of the antibody under conditions sufficient for the antibody to bind the epitope to produce bound antibody. The method also includes contacting the bound antibody with one or more biocatalyst-linked antibodies, or biocatalyst-linked antigen binding portions thereof, that bind to the bound antibody under conditions sufficient for the one or more biocatalyst-linked antibodies, or the biocatalyst-linked antigen binding portions thereof, to bind to the bound antibody to produce a binding complex, wherein the biocatalyst catalyzes the conversion of at least one substrate into at least one detectable reagent. In addition, the method also includes contacting the binding complex with the substrate under conditions sufficient for the biocatalyst to convert the substrate to the detectable reagent, and detecting the detectable reagent, thereby detecting the antibody to the pathogen in the sample. In some embodiments, the pathogen comprises a severe acute respiratory syndrome coronavirus-2 (SARS-CoV-2). In some embodiments, the biocatalyst comprises invertase.

In another aspect, the present disclosure provides a method of detecting a severe acute respiratory syndrome coronavirus-2 (SARS-CoV-2) antibody in a sample. The method includes contacting the sample with an epitope of the SARS-CoV-2 antibody under conditions sufficient for the SARS-CoV-2 antibody to bind the epitope to produce bound SARS-CoV-2 antibody. The method also includes contacting the bound antibody with one or more invertase-linked antibodies, or invertase-linked antigen binding portions thereof, that bind to the bound SARS-CoV-2 antibody under conditions sufficient for the one or more invertase-linked antibodies, or the invertase-linked antigen binding portions thereof, to bind to the bound SARS-CoV-2 antibody to produce a binding complex. The method also includes contacting the binding complex with sucrose under conditions sufficient for the invertase to convert the sucrose to fructose and glucose, and detecting the fructose and/or the glucose, thereby detecting the SARS-CoV-2 antibody in the sample. In some embodiments, the method further includes contacting the binding complex with one or more angiotensin-converting enzyme 2 (ACE2) receptors. In some embodiments, the method further includes contacting the binding complex with one or more invertase-ACE2 receptor conjugates. In some embodiments, the method further includes obtaining the sample from a test subject. In some embodiments, the sample comprises an oral fluid sample obtained from a test subject.

In another aspect, the present disclosure provides a microfluidic device, comprising a body structure having at least one inlet port and at least one outlet port that are in fluid communication with one another via at least one channel at least partially defined by the body structure, which body structure comprises at least a portion of a first reservoir that comprises a sucrose solution, at least a portion of a second reservoir that comprises a solution of one or more invertase-linked antibodies, or invertase-linked antigen binding portions thereof, that bind to a severe acute respiratory syndrome coronavirus-2 (SARS-CoV-2) antibody, at least a portion of a flow resistor region that comprises immobilized epitopes of the SARS-CoV-2 antibody, and at least a portion of a fluid conveyance mechanism, wherein the first reservoir, the second reservoir, the flow resistor region, and the fluid conveyance mechanism are in fluid communication with the at least one channel. In some embodiments, the flow resistor region comprises an assay pad (e.g., a hydrogel or the like). In some embodiments, a kit includes the microfluidic device. In some embodiments, the kit further includes a glucometer (e.g., integrated within the microfluidic device or included as a separate kit component). In some embodiments, the kit further includes an oral fluid collector.

In another aspect, the present disclosure provides a reaction mixture that includes sucrose, one or more invertase-linked antibodies, or invertase-linked antigen binding portions thereof, that bind to a severe acute respiratory syndrome coronavirus-2 (SARS-CoV-2) antibody, and the SARS-CoV-2 antibody. In some embodiments, the kit further includes an epitope of the SARS-CoV-2 antibody.

In another aspect, the present disclosure provides a system that includes a fluid control device, comprising a body structure having at least one inlet port and at least one outlet port that are in fluid communication with one another via at least one channel at least partially defined by the body structure, which body structure comprises at least a portion of a first reservoir that comprises a sucrose solution, at least a portion of a second reservoir that comprises a solution of one or more invertase-linked antibodies, or invertase-linked antigen binding portions thereof, that bind to a severe acute respiratory syndrome coronavirus-2 (SARS-CoV-2) antibody, at least a portion of a flow resistor region that comprises immobilized epitopes of the SARS-CoV-2 antibody, and at least a portion of a fluid conveyance mechanism, wherein the first reservoir, the second reservoir, the flow resistor region, and the fluid conveyance mechanism are in fluid communication with the at least one channel. The system also includes a detection device in fluid communication with the outlet port, which detection device is configured to detect glucose and/or fructose. The system also includes a control device operably connected to the detection device, which control device comprises, or is capable of accessing, computer readable media comprising non-transitory computer-executable instructions which, when executed by at least one electronic processor perform at least: detecting the glucose and/or the fructose, when the invertase converts the sucrose to the glucose and/or the fructose.

BRIEF DESCRIPTION OF THE DRAWINGS

The accompanying drawings, which are incorporated in and constitute a part of this specification, illustrate certain embodiments, and together with the written description, serve to explain certain principles of the methods, devices, kits, reaction mixtures, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DEFINITIONS

Figure 1:
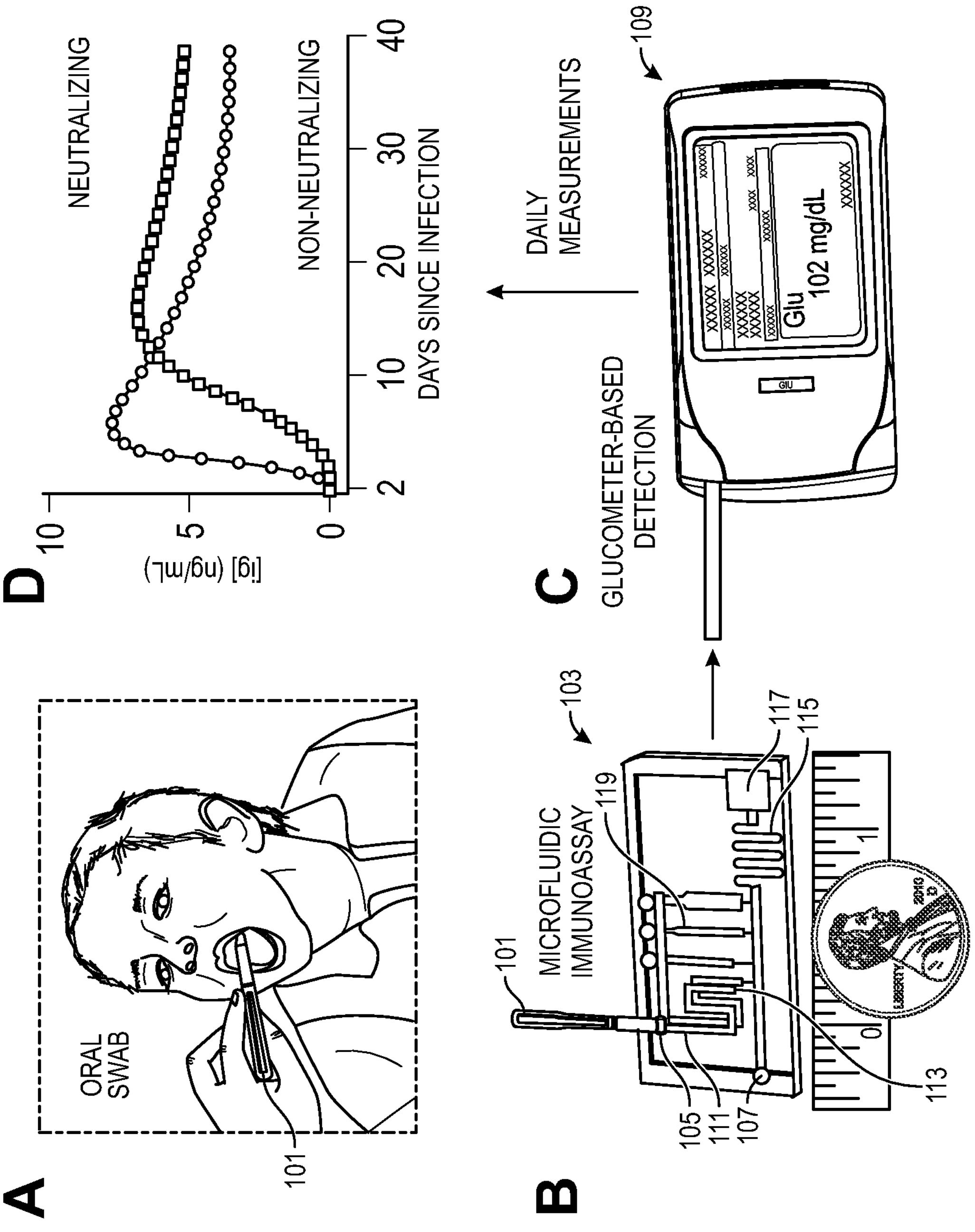
FIG. 1 (panels A-D) schematically shows a platform for decentralized detection of SARS-CoV-2 antibodies at the population scale. In some embodiments, the platform provides a non-invasive, convenient, and cost-effective detection approach that leverages various technologies to achieve highly specific and sensitive detection of SARS-CoV-2 antibodies at a population scale.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Administering: As used herein, the terms "administering" and "administration" refer to any method of providing a pharmaceutical preparation or other treatment to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Angiotensin-Converting Enzyme 2: As used herein, "angiotensin-converting enzyme 2" or "ACE2" refers to a zinc containing metalloenzyme that binds or otherwise associates with coronavirus, such as SARS-CoV-2. In some embodiments, ACE2 is used as a cognate receptor of SARS-CoV-2 in the pathogen detection devices and systems disclosed herein.

Antibody: As used herein, the term "antibody" refers to an immunoglobulin or an antigen-binding domain thereof. The term includes but is not limited to polyclonal, monoclonal, monospecific, polyspecific, non-specific, humanized, human, canonized, canine, felinized, feline, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda. The term "monoclonal antibody" refers to an antibody that displays a single binding specificity and affinity for a particular target, e.g., epitope.

Antigen Binding Portion: As used herein, the term "antigen binding portion" refers to a portion of an antibody that specifically binds to an epitope of an antibody to a pathogen (e.g., a severe acute respiratory syndrome coronavirus-2 (SARS-CoV-2)), e.g., a molecule in which one or more immunoglobulin chains is not full length, but which specifically binds to the antibody to the pathogen. Examples of binding portions encompassed within the term "antigen-binding portion of an antibody include (i) a Fab fragment, a monovalent fragment consisting of the VLC, VHC, CL and CH1 domains: (ii) a F(ab')2 fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment, which consists of a VHC domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFV). Such single chain antibodies are also encompassed within the term "antigen binding portion" of an antibody. These antibody portions are obtained using conventional techniques known to those with skill in the art, and the portions are screened for utility in the same manner as are intact antibodies.

Bind: As used herein, "bind," in the context of pathogen detection, refers to a state in which a first chemical structure (e.g., a pathogenic particle) is sufficiently associated a second chemical structure such that the association between the first and second chemical structures can be detected.

Communicate: As used herein, "communicate" refers to the direct or indirect transfer or transmission, and/or capability of directly or indirectly transferring or transmitting, something at least from one area to another area.

Conjugate: As used herein, "conjugate" or "linked" refers to a reversible or irreversible connection between two or more substances or components. In some embodiments, for example, biocatalysts (e.g., enzymes) are connected to antibodies and/or to antigen binding portions thereof. In some embodiments, biocatalysts are conjugated with antibodies and/or to antigen binding portions thereof via one or more linker compounds.

Detecting: As used herein, "detecting," "detect," or "detection" refers to an act of determining the existence or presence of one or more target analytes (e.g., pathogenic particles, such as severe acute respiratory syndrome coronavirus-2 (SARS-CoV-2) particles) in a sample.

Epitope: As used herein, "epitope" refers to the part of an antigen (e.g., an antibody to a pathogen) to which an antibody and/or an antigen binding portion binds.

Pathogen: As used herein, "pathogen" or "pathogenic particle" refers to anything that can produce a disease, condition, or disorder in a subject. In some embodiments, a pathogen includes an infectious microorganism or agent, such as a bacterium, virus, viroid, protozoan, prion, or fungus.

Reaction Mixture: As used herein, "reaction mixture" refers a mixture that comprises molecules and/or reagents that can participate in and/or facilitate a given reaction or assay. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction or assay components.

Receptor: As used herein, "receptor" refers to a biochemical structure that receives or binds other biochemical structures (e.g., pathogenic particles).

Sample: As used herein, "sample" means anything capable of being analyzed using a device or system disclosed herein. Exemplary sample types include environmental samples and biological samples. In some embodiments, subjects exhale, spit, sneeze, cough, and/or the like to produce aerosolized samples.

Severe Acute Respiratory Syndrome Coronavirus-2: As used herein, "severe acute respiratory syndrome coronavirus-2" or "SARS-CoV-2" refers to the coronavirus that emerged in 2019 to cause a human pandemic of an acute respiratory disease, now known as coronavirus disease 2019 (COVID-19).

Specifically Bind: As used herein, "specifically bind," in the context of pathogen detection, refers to a state in which substantially only target chemical structures (e.g., target pathogenic particles) are sufficiently associated with a corresponding or cognate binding agent, to the exclusion of non-target chemical structures, such that the association between the target chemical structures and the binding agent can be detected.

System: As used herein, "system" in the context of analytical instrumentation refers a group of objects and/or devices that form a network for performing a desired objective.

Subject: As used herein, "subject" refers to an animal, such as a mammalian species (e.g., human) or avian (e.g., bird) species. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject." For example, a subject can be an individual who has been diagnosed with having a respiratory disease, disorder, or condition, is going to receive a therapy for a respiratory disease, disorder, or condition, and/or has received at least one therapy for a respiratory disease, disorder, or condition.

Therapy: As used herein, "therapy" or "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human.

DETAILED DESCRIPTION

Motivated at least in part by the need to produce convenient diagnostic platforms for the monitoring of infection spread at population scale, some embodiments of the present disclosure provide a disposable electrochemical diagnostic platform that is autonomous and self-contained, and that leverages certain technologies to detect SARS-CoV-2 antibodies (FIG. 1). In some embodiments, the approach includes three readily deployable elements: (1) a non-invasive oral fluid collector (101), (2) an autonomous microfluidic device (103) with entry (105) and outlet (107) ports for specimen delivery and analysis; and (3) a glucometer (109). By using advanced, ultrasoft swabs to painlessly collect oral fluid, the approach allows for convenient testing in people of all ages (FIG. 1A). In some of these embodiments, these swabs are supported by a toothbrush-like handle with a connector to be inserted into the entry port of the microfluidic device (FIG. 1B). In the embodiment shown, microfluidic device 103 also includes reservoir 111, trigger valve 113, flow resistor 115, capillary pump 117, and retention burst valve 119. In some embodiments, this device serially controls the passage of specimen and reagent solutions over an immunoassay pad, which contains enzymes catalyzing the production of glucose proportionally to the number of SARS-CoV-2 antibodies present in the specimen. In some embodiments, the glucose is detected at an outlet port via a glucometer (FIG. 1C). Such a detection approach is unparalleled and enables serial monitoring of antibody titers in individuals, empowering scientists and clinicians with rapid, quantitative information regarding immunity (FIG. 1D). Moreover, the convenient design of each element allows large-scale manufacturing and, thus, readily enables SARS-CoV-2 infection monitoring at, for example, the population scale.

In some embodiments, the present disclosure fulfills a need for decentralized, low-cost, safe, and convenient diagnostic devices achieving rapid and accurate population-scale identification of individuals who are positive for SARS-CoV-2 antibodies in order to monitor and mitigate viral spread. One exemplary approach to produce a device capable of being deployed broadly to clinics, hospitals, community centers, and at home is to adapt established detection technologies to the measurement of virus-targeting antibodies. Following this reasoning, in some embodiments, the methods and related aspects of the present disclosure combine a sandwich immunoassay with electrochemical detection via a glucometer, integrated into an autonomous and disposable fluidic cartridge (FIG. 1B, C).

In some embodiments, the platform disclosed herein enables widespread detection of SARS-CoV-2-targeted antibodies in both symptomatic and asymptomatic individuals. Thus, deployment of the present technology enables true population scale assessment of COVID-19 spread and immunity. This can support, for example, efforts to restart industrial, academic, and other economic activities that need continuing, frequent, and repetitive testing of personnel and clientele for anti-SARS-CoV-2 antibodies. Moreover, continuous disease monitoring facilitates contact tracing and similar efforts to contain the spread of infection. In some embodiments, large-scale deployment of specific and sensitive serology assays complements reverse transcription polymerase chain reaction (RT-PCR) testing approaches and informs on the appropriate frequency of viral antigen screening to control disease dissemination. In some embodiments, the modular platform disclosed herein can be readily adapted for the detection and mitigation of other viral epidemics through straightforward substitution of the capture antigen employed in the immunoassay.

The platform and related aspects disclosed herein overcome various limitations of pre-existing antibody detection platforms, including, for example:

1. The specimen collection approach is painless and not invasive (FIG. 1A), thus supporting facile antibody detection in both normal and vulnerable populations. This feature contrasts with benchmark serology measurements, which still require blood draws and specimen processing prior to detection.
2. The fluidic device is portable, disposable and autonomous (FIG. 1B), offering a fully decentralized detection approach that does not require trained personnel, minimizes or eliminates test-related exposures, and enables at-home monitoring of seroconversion. This element is unparalleled in current diagnostic platforms and achieves population-scale monitoring of immunity.
3. The present detection assay is specifically customized to detect both antibody binding and neutralization, offering direct measurement of the development of immunity in a decentralized format for the first time. By contrast, pre-existing serological assays are designed to detect only antibody binding, and consequently offer an indirect, inaccurate, and incomplete measure of immunity.
4. In some embodiments, the detection method is electrochemical, overcoming limitations related to background fluorescence emission or color that frequently plague optical detection approaches. Moreover, because the level of current produced in the assay is directly proportional to antibody concentration, the approach is quantitative and does not depend on band interpretation, as do highly inaccurate lateral flow assays.
5. Because the detection approach is based on glucose measurements (FIG. 1C), the platform is compatible with widely available and commercially successful glucometers, facilitating scalable deployment for at-home use, even in remote areas.

Together, these exemplary innovations culminate in a paradigm-altering technology for the decentralized measurement of immunity that readily supports frequent and repetitive measurements of antibody titers at population scale (FIG. 1D).

Figure 2:
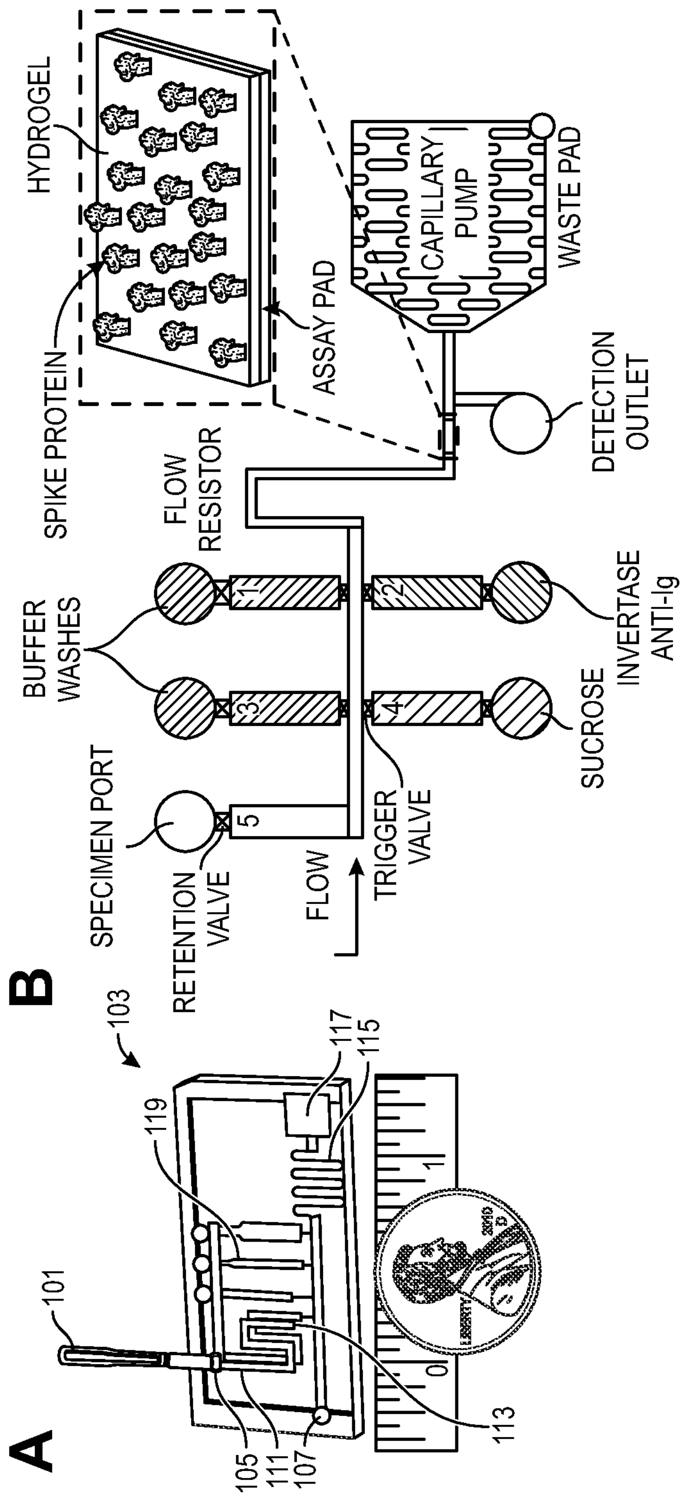
FIG. 2 (panels A and B) schematically shows an exemplary microfluidic platform design according to some embodiments. (A) Some embodiments include a pocket-size, disposable microfluidic device that autonomously processes oral fluid specimens to achieve SARS-CoV-2 antibody detection. Here is shown an at-scale example of one device. Note that this design can be readily adapted to accommodate the antibody detection methods disclosed herein. (B) Schematic representation of the self-powered microfluidic liquid handling device that manipulates 5 solutions in a pre-programmed, autonomous, sequential manner. When the specimen is injected into the circuit via the entry port, the specimen will slowly flow towards the capillary pump due to capillary effects. As the specimen reaches the pump, the flow is activated in the channel and disrupts the pressure balance within the device. The negative pressure created by the fluid conveyance mechanism (e.g., a capillary pump) sequentially activates retention burst valves, thereby injecting reagents into the assay pad. The pad is functionalized with the full-length SARS-CoV-2 spike protein to enable capture of patient IgA, IgM, and IgG. To specifically identify neutralizing antibodies, competitive assays are implemented that involve the use of human ACE2, the receptor through which spike protein enters host cells.

In some embodiments, the platform is a disposable plastic capillary channel with a detector (FIG. 2). In these embodiments, the device includes the components:

[1] Oral fluid collector. In some embodiments, the decentralized diagnostic assay uses gum swabs to extract oral fluid from subjects. Saliva specimens contain high levels of immunoglobulin (Ig) A, IgM, and IgG against SARS-CoV-2, which can be detected via immunoassays. In some embodiments, the specimen collection approach employs a synthetic, ultra-soft swab, which is designed to extract saliva from the gums while minimizing levels of contaminants and filtering out mucins, cells, and other aggregates. The swabs are supported by a disposable plastic handle that allows them to be used like toothbrushes. After rubbing the gums with a swab for ~5 minutes (FIG. 1A), the swab is placed inside a receptacle adapted to fit the platform. Screwing the receptacle onto the fluidic device (FIG. 1B) delivers a precise volume, activating detection.

[2] Microfluidic device. In some embodiments, the channel in the device (FIG. 2A, B) controls five fluids (labelled 1-5) in a pre-programmed, autonomous, sequential manner. In some embodiments, this fluidic system exploits the capillary phenomenon—an interplay between surface tension and channel geometry—to spontaneously fill channels. When a specimen is delivered to the inlet port of the device (labelled as 5 in FIG. 2B), the contact angle between the specimen (liquid) and the channel walls (solids) determines the capillary pressure across the channel. Wetting the channel walls with the specimen (contact angle <90°) generates negative pressure in the front end of the liquid, driving the specimen to flow, passing a detector zone toward a capillary pump. As the specimen reaches the capillary pump, the pump is activated to maintain a negative pressure gradient across the specimen meniscus, disrupting the capillary pressure balance within the device. The pre-filled reagents in branches are held stationary due to balanced capillary pressures between two meniscuses formed at the opposite ends of the reagent reservoirs (junction and injection port). When the capillary pump is activated, the capillary pressure at the junctions branching into the main channel uniformly and continuously decreases for all reagents. On the other hand, the capillary pressure created by the other end of the branch for each reagent remains constant at the predetermined level based on the retention burst valve geometry and surface tension of the reagent. As such, the pressure drop across each reagent reservoir can be fine-tuned to a monotonically decreasing threshold pressure, activating the retention burst valves for solutions 1, 2, 3, and 4. This pressure at the junction between the main channel and reagent branches sequentially activates retention burst valves, thereby releasing and flowing reagents over the detector region. While the capillary pump sustains flow, the injection speed and sequence of reagents are regulated by the geometry and arrangements of capillaric elements (e.g., fluidic resistor, valves, and reservoir geometry).

Figure 3:
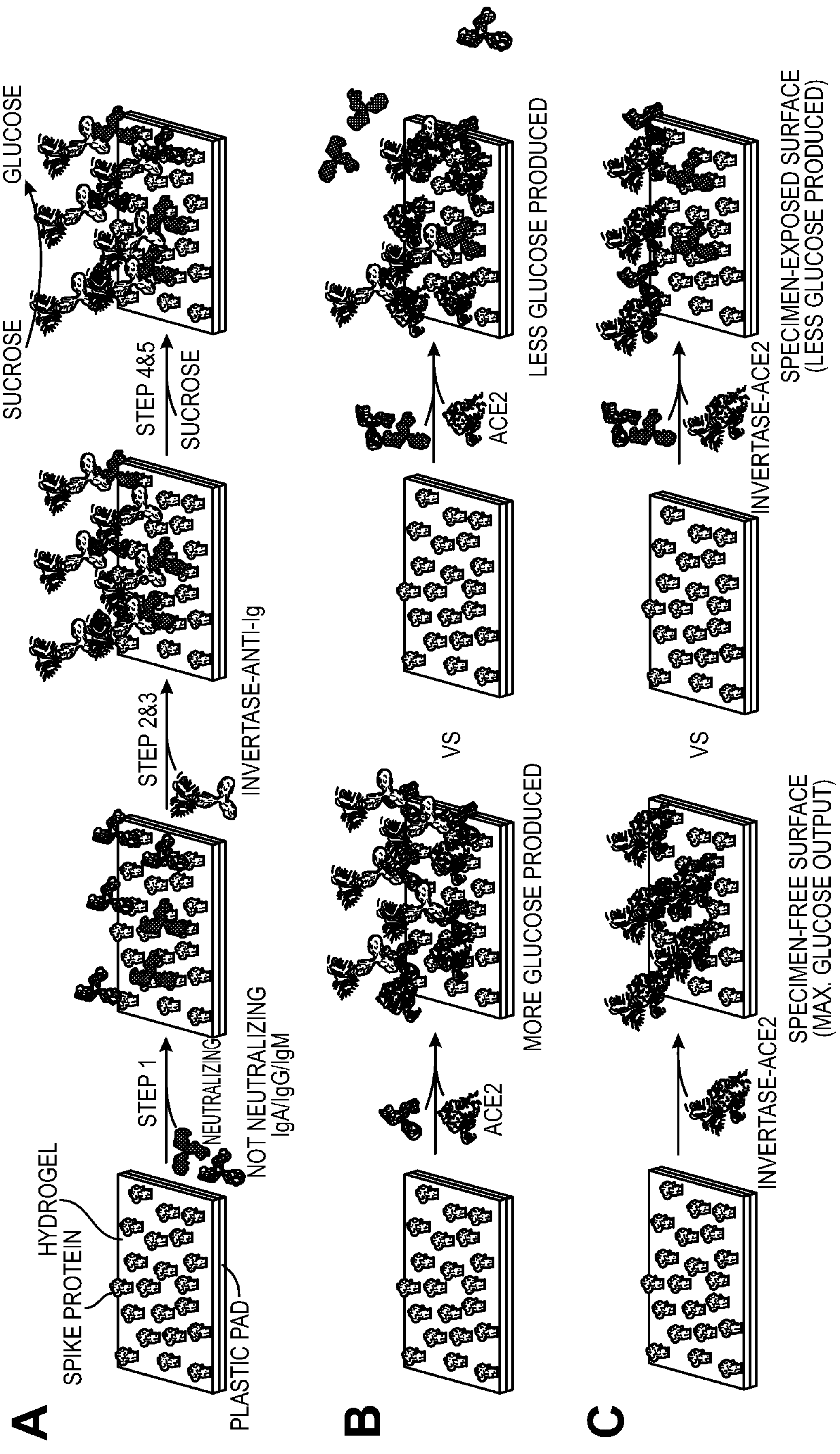
FIG. 3 (panels A-C) schematically shows exemplary detection assays. In some embodiments, the assay pad will consist of a plastic base coated with an antifouling hydrogel. The hydrogel will be functionalized with full-length SARS-CoV-2 spike protein to enable the capture of patient immunoglobulins. (A) The general detection approach for all SARS-CoV-2 antibodies is a 5-step sandwich immunoassay. The incubation time in each step is tuned to achieve detection within 1 hour. The reporter system is an invertase-conjugated anti-Ig antibody, which binds to patient-derived SARSCoV-2 IgA/IgM/IgGs, if present. Bound invertase catalyzes the conversion of sucrose to glucose, which is delivered to the detection outlet (FIG. 2B) of the device for electrochemical readout via a glucometer. Both the presence and amount of SARS-CoV-2 antibodies in the specimen can be extrapolated from the current readout. In some embodiments, two neutralization assays are used: (B) The Type I competition assay has ACE2 added to the specimen containing SARS-CoV-2 antibodies. Neutralizing antibodies (orange), if present, will compete with ACE2 for binding to the immobilized spike protein. Therefore, a comparison between specimens in the absence versus presence of ACE2 will provide a relative measure of neutralizing antibody levels. (C) The Type II assay uses invertase-ACE2 conjugates, instead of invertase-anti-Ig, to specifically report on ACE2 binding to immobilized spike protein. In the absence of specimen, the conjugate will saturate immobilized spike protein, marking the maximum signal output of the assay. However, the presence of neutralizing antibodies in the specimen will interfere with invertase-ACE2 binding to spike protein, reducing the signal output of the assay. If neutralizing antibodies bind with a too high affinity to the spike protein for ACE2 to effectively compete, they may not be quantifiable by the Type I assay, but these antibodies will be quantified using the Type II assay.

[3] Glucometer detection. In some embodiments, the detection mechanism is a 5-step sandwich immunoassay (FIG. 3A): In step 1, a specimen is made to flow over the assay pad, and SARS-CoV-2 antibodies (IgA/IgM/IgG) contained in the specimen bind to the surface-attached spike protein. Step 2 is a wash. In step 3, a solution of invertase enzyme conjugated to an anti-human IgA/IgM/IgG antibody is made to flow over the pad. The invertase-anti-Ig conjugate binds to captured patient-derived SARS-CoV-2 antibodies (IgA/IgM/IgG), if present. Step 4 is a wash. In step 5, a solution of sucrose is made to flow over the detector. Bound invertase immediately catalyzes the conversion of sucrose to glucose, which is delivered to the detection outlet for electrochemical readout via a glucometer. The current readout is produced by the glucose oxidase-catalyzed oxidation of glucose via the cofactor flavin adenine dinucleotide (FAD/$FADH_2$), which is buried within the enzyme and facilitates efficient transfer of electrons to a redox mediator and then to a sensing electrode. Electrons then move from the sensing electrode through wiring to a counter electrode that delivers them via anions to the original solution, thus completing an electrical circuit. The current readout is thus proportional to the amount of glucose produced by the invertase catalyzed reaction.

In some embodiments, the detection assays are supported on a plastic pad coated with an antifouling hydrogel (FIG. 3A). The latter is typically used to prevent non-specific binding of biomolecules to the pad. In some embodiments, the hydrogel is functionalized with SARS-CoV-2 full spike protein (extracellular domain) to enable the capture of patient IgA, IgM, and IgG. In one assay embodiment (FIG. 3A), patient samples are applied to pads, and a detection (secondary) anti IgA/IgM/IgG antibody conjugated to invertase is applied to those pads. Then, the pads are assayed for their ability to catalyze sucrose-to-glucose conversion. This provides a measure of total antibody concentration in the patient samples, without discriminating between antibody class types. In a second assay, angiotensin converting enzyme (ACE2) is used, the receptor through which the SARS-CoV-2 virus enters host cells, to detect the presence of neutralizing antibodies. For this assessment, two exemplary assay types are used. In the Type I assay (FIG. 3B), a pre-set amount of ACE2 is added to patient specimens; SARS-CoV-2 antibodies that are neutralizing will compete with ACE2 for binding to the immobilized spike protein. The proportions of antibodies that bind to spike protein in the absence versus presence of ACE2 are assayed by measuring the sucrose-to-glucose catalytic activity of invertase conjugated to secondary anti-IgA/IgM/IgG antibody. Comparison of these results reports the presence of neutralizing antibodies. Furthermore, a complementary quantitative Type II assay can be performed by employing invertase conjugated to ACE2 instead of the anti-IgA/IgM/IgG antibody (FIG. 3C). Reduction in enzyme-ACE2 conjugate-mediated glucose conversion "with" versus "without" patient specimen is measured to determine the levels of neutralizing antibody in a given patient sample. To summarize, in some embodiments, the platform achieves antibody detection and neutralization assessment via sandwich immunoassays, in which SARS-CoV-2 spike protein is used as a surface-bound capture agent in the first layer. The second layer is patient IgA, IgM, and IgG originating from the oral fluid specimen. The third layer contain an enzymatic reporter, invertase, covalently conjugated to an anti-IgA/IgM/IgG antibody (or conjugated to ACE2 in the case of the Type II competitive assay).

Figure 4:
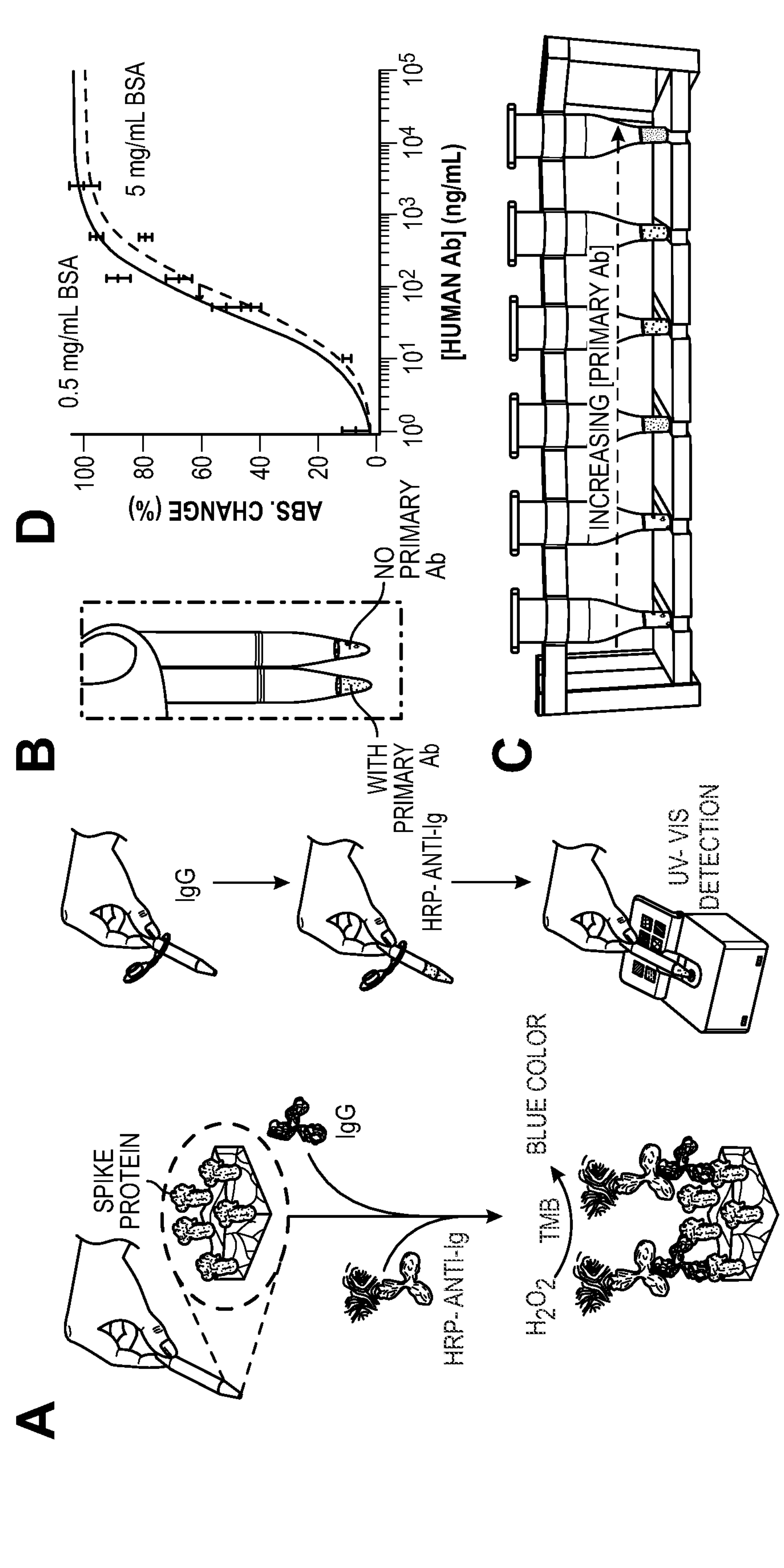
FIG. 4 (panels A-D) schematically show antifouling hydrogels support affinity-based sensing on plastic. In some embodiments, a sandwich immunoassay is used for detection of SARS-CoV-2 antibodies. Using monoclonal anti-SARS-CoV-2 antibodies (IgG), and spike protein, a colorimetric assay has been developed. (A) In this assay, spike protein is immobilized within the BSA-GA hydrogel using carbodiimide coupling chemistry, creating a covalent bond between the protein and hydrogel. The reporter is HRP, an enzyme that catalyzes the reduction of hydrogen peroxide to water using tetramethylbenzidine (TMB) as a mediator, which turns blue upon being oxidized by the enzyme. (B) Using this assay, the effectiveness of the antifouling gel at preventing non-specific adsorption of secondary antibodies on the plastic supports has been demonstrated. (C) The oxidation of TMB generates a blue color (here faded because of the camera flash exposure) in solution that monotonically increases in intensity with increasing concentrations of positive sandwich immunoassays on the plastic surface. (D) Using absorbance measurements and this assay, the concentration of BSA within the gels reporting the highest affinity for the antibody assay was determined.

The functionalization of plastic pads with antifouling hydrogels has been demonstrated. As a starting point, bovine serum albumin (BSA) and glutaraldehyde (GA) were employed to form heavily crosslinked hydrogels on the surface of laser-cut plastic strips (FIG. 4). These hydrogels have been demonstrated to support fouling-free affinity sensing. The strips were made of poly(methyl methacrylate), the same material that can be used for fabrication of the fluidic devices. To evaluate the functionality of the hydrogels, a colorimetric sandwich immunoassay was employed using anti-SARS-CoV-2 antibodies and full spike protein (FIG. 4A). The reporters in this assay were horse radish peroxidase (HRP)-conjugated anti-Ig antibodies. HRP is an enzyme that catalyzes the reduction of hydrogen peroxide to water using tetramethylbenzidine (TMB) as a mediator, which turns blue upon being oxidized by the enzyme. When the hydrogels were functionalized with spike protein and exposed to primary (monoclonal human IgG) and secondary antibodies (anti human IgG), they turned blue as expected; however, the same was not true in the absence of primary antibodies (FIG. 4B), indicating that the hydrogel effectively blocks non-specific binding. Using this platform, immunoassay calibration experiments have been performed that show a monotonic correlation between the concentration of primary antibody and enzyme activity (FIG. 4C). These measurements have allowed for the optimization of the concentration of hydrogel elements to achieve maximum sensitivity in the immunoassay (FIG. 4D). Building on these preliminary results, a different reporter based on the enzyme invertase to enable electrochemical detection of SARS-CoV-2 antibodies using a glucometer is optionally used as described further herein.

Figure 5:
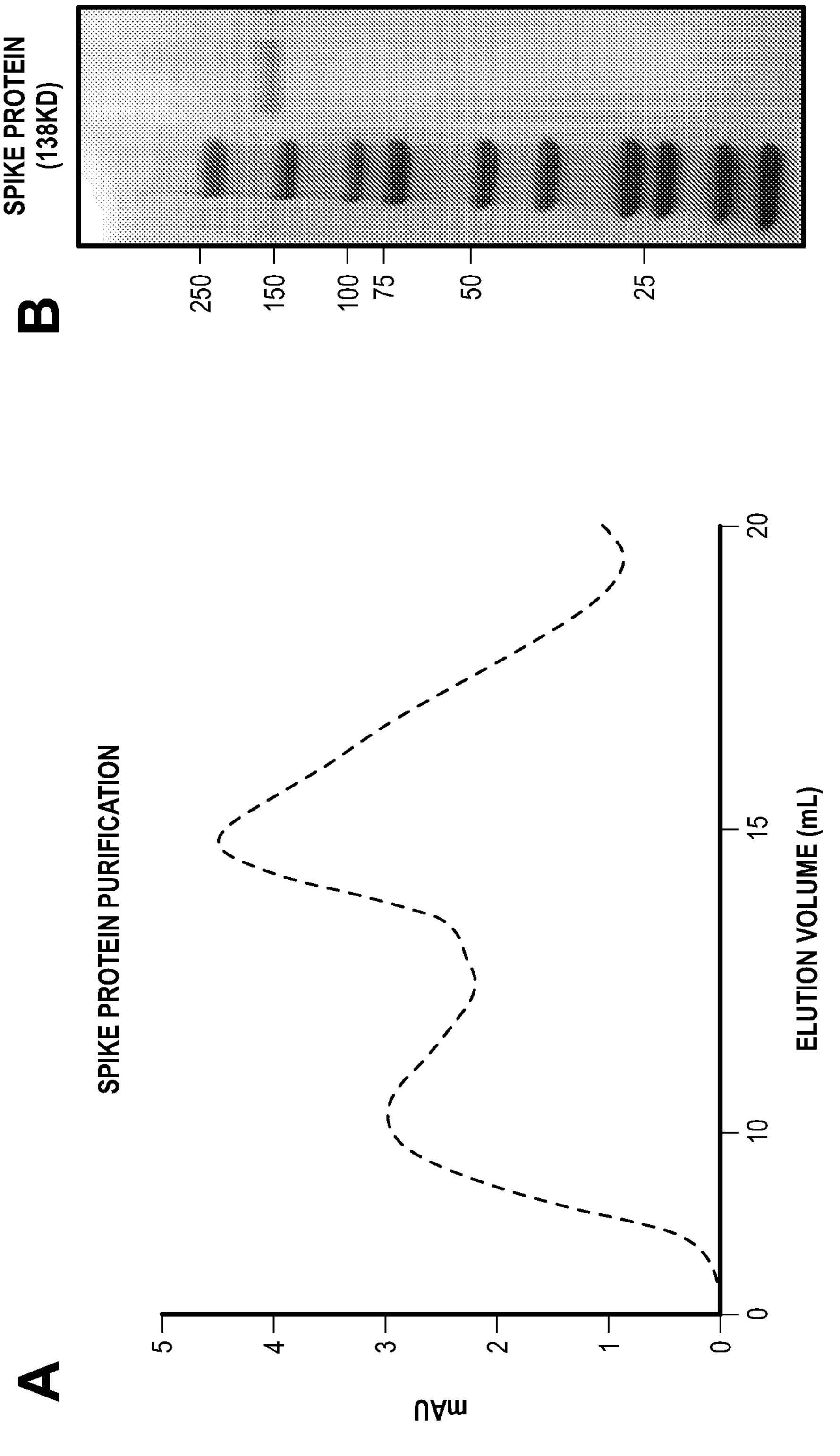
FIG. 5 (panels A and B) schematically show purification of SARS-CoV-2 spike protein. (A) The full-length extracellular domain of the SARS-CoV-2 spike protein was purified from a mammalian cell expression system. A representative size exclusion chromatography trace is shown. The first peak represents the spike protein. (B) Non-reducing SDS-PAGE analysis of recombinantly produced spike protein.

Protocols have been established to recombinantly produce the full extracellular domain (ECD) of the SARS-CoV-2 spike protein containing 2 stabilizing mutations (K986P and V987P) and with the furin cleavage site mutated from RRAR to A. The gene encoding the stabilized SARS-CoV-2 spike protein ECD followed by a hexahistidine tag was cloned into a mammalian expression plasmid. The plasmid was transiently transfected into human embryonic kidney (HEK) 293F cells, and secreted spike protein was purified from cell supernatants 5 days post transfection via Ni-NTA affinity chromatography followed by size-exclusion chromatography on a fast protein liquid chromatography (FPLC) instrument (FIG. 5A). Purity (>99%) and size were confirmed via SDSPAGE analysis (FIG. 5B).

Yields of the full-length spike protein ECD were relatively modest (<100 μg/L); thus, production can be improved through modification of the spike ECD with 4 proline mutations (F817P, A892P, A899P, and A942P) that were recently demonstrated to enhance protein expression by 10-fold. The expression medium and purification conditions can be optimized to maximize protein isolation.

Figure 6:
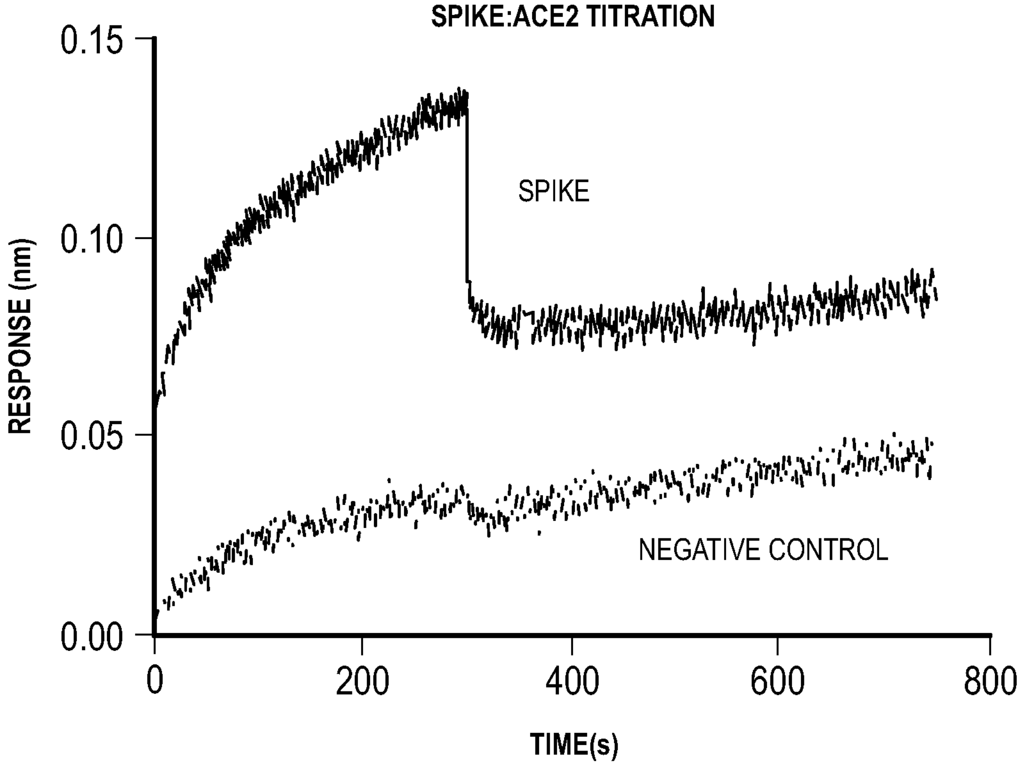
FIG. 6 is a plot showing recombinantly produced spike protein binding ACE2. ACE2 was immobilized, and binding of recombinantly produced SARS-CoV-2 spike protein extracellular domain (spike) was measured via bio-layer interferometry analysis. Note that significant binding was observed compared to a negative control protein.

Purified spike protein can be characterized via bio-layer interferometry studies using an Octet® instrument (Molecular Devices). Biotinylated ACE2 can be purchased commercially (Sino Biological) and immobilized on streptavidin-coated tips. Recombinantly produced spike protein can be titrated against ACE2 and compared to commercial spike protein to validate function. It was confirmed that the SARS-CoV-2 spike protein ECD specifically binds to ACE2 via biolayer interferometry (FIG. 6).

Figure 9:
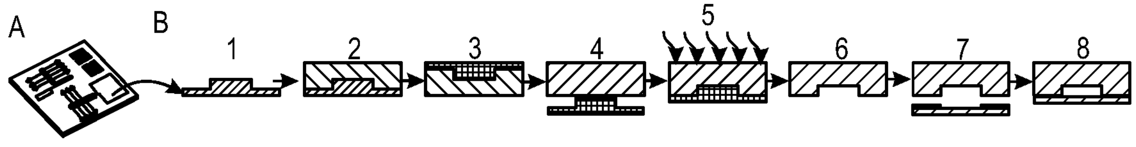
FIG. 9 (panels A and B) schematically shows an exemplary fabrication of a microfluidic platform. (A) High-resolution 3D printing can be used to produce hard molds of the microfluidic device. (B) In some embodiments, the fabrication process consists of (1) SLA 3D print of feature mold. (2) The casting of PDMS mold (top portion). (3) Casting of high temperature epoxy mold from PDMS (top portion). (4-6) Application of high temperature and pressure to hot emboss PMMA with epoxy mold. (7) Application of adhesive on flat PMMA sheet. (8) Bonding with patterned PMMA yields an enclosed microfluidic chip.

Protocols to functionalize the assay pad (FIG. 2B) with spike protein are developed. Chemistries that allow effective coating of plastic strips with antifouling hydrogels and spike protein (FIG. 4B) have been established, such chemistries can be adapted to the geometry and dimensions of the assay pad to be integrated into the microfluidic device. The assay pad can be formed by hot embossing a rectangular trench on the plastic base of the fluidic platform (see step 7 in FIG. 9). The depth of this trench can be adapted to match the hydrogel's thickness, measured via profilometry or atomic force microscopy, to prevent any unintended flow-interference caused by hydrogel protrusion into the channel. Hydrogel density and composition can be optimized for compatibility with low temperature-bonding of the top and bottom parts of the device. The performance of the hydrogels can be evaluated by conducting immunoassays (FIG. 4B-D).

The loading concentration of spike protein that results in the full conversion of sucrose to glucose when bound to invertase-antibody conjugates can be determined. To load the protein into the hydrogel, carboxylic groups naturally present in BSA can be activated via carbodiimide (EDC) coupling. The reaction proceeds in the presence of N-hydroxysuccinimide (NHS), which forms a stable NHS ester intermediate that can be efficiently conjugated to primary amines available on the surface of the spike protein.

To establish the enzyme/antibody fusion for a sandwich assay, invertase, the enzyme that catalyzes the conversion of sucrose to glucose, can be chemically linked to an antibody that recognizes human IgA, IgM, and IgG. Following the approach that was previously implemented for glucometer-based detection of small molecules and proteins, Saccharomyces cerevisiae-derived invertase (Sigma) can be conjugated to a commercial antihuman IgA/IgM/IgG antibody (Southern Biotech). Enzyme-antibody conjugation can be implemented using sulfosuccinimidyl 4-[N-maleimidomethyl]cyclohexane-1-carboxylate (sulfo-SMCC) chemistry (Fisher Scientific), according to the manufacturer's protocol.

Following conjugation, functionality of the antibody can be confirmed by enzyme-linked immunosorbent assay (ELISA), using plates coated with human IgG, and invertase functionality can be assessed by sucrose conversion, comparing conjugated material to free enzyme.

Figure 7:
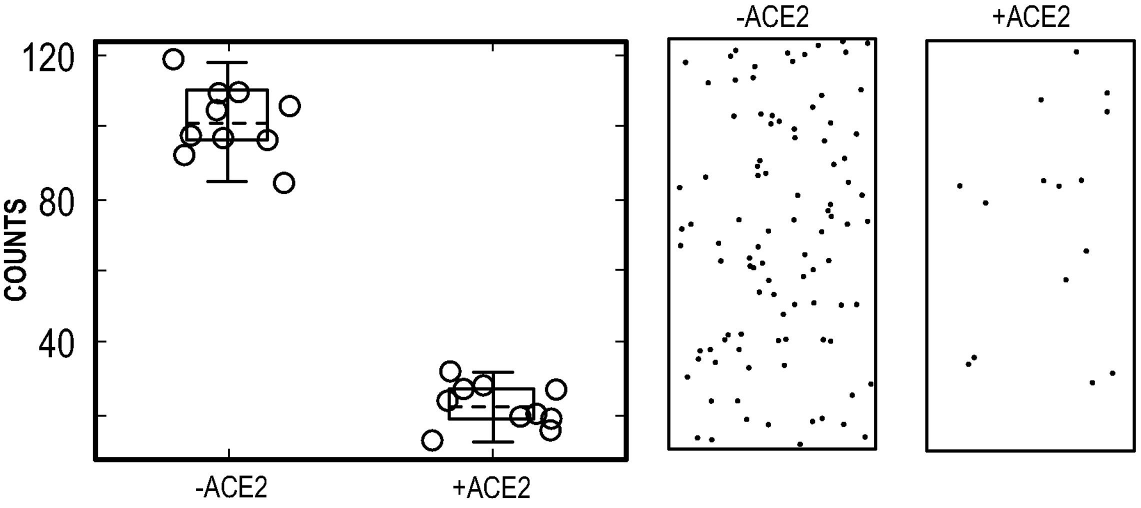
FIG. 7. Assaying for neutralizing antibodies using ACE2. Biotinylated-RBD (receptor binding domain of spike protein) was immobilized on a neutravidin coated slide, followed by binding of primary antibody to RBD and then a fluorescently labeled secondary antibody. Unbound protein was washed away. In another channel on the same slide, the assembly was further incubated with ACE2 for 10 mins, before washing and imaging. Counts are the number of fluorescent spots (corresponding to fluorescently labeled secondary antibodies) in fields of view. 10 fields of view were recorded for either case. Dashed bars represent the medians, the boxes extend from the 25th to 75th percentile, and whiskers cover the full data range. Example fields of view showing fluorescent spots are shown at right. Successful ACE2 competition validates the Type I assay design.

Neutralizing antibodies present in the specimen can interfere with ACE2 binding to the hydrogel immobilized SARS-CoV-2 spike protein. To detect the fractional concentration of these antibodies, two assays can be used. The Type I competition assay (FIG. 3B) has ACE2 added to the human specimen containing SARS-CoV-2 antibodies. Neutralizing antibodies, if present, compete with ACE2 for binding to the immobilized spike protein. Therefore, a comparison between specimens in the absence versus presence of ACE2 provides a relative measure of neutralizing antibody levels in the specimen (i.e., signal from the invertase-anti-Ig conjugate decreases in the presence of ACE2 if neutralizing antibodies are present). To illustrate the operation of this assay type, ultrasensitive single-molecule fluorescence microscopy was used to demonstrate that soluble ACE2 reduces the number of interactions between the hydrogel immobilized spike protein and anti-spike neutralizing antibodies by a factor of four (FIG. 7).

To complement the Type I assay, the Type II competition assay can be implemented (FIG. 3C). The Type II assay uses invertase-ACE2 conjugates, instead of invertase-anti-Ig, to specifically report on ACE2 binding to immobilized spike protein. In the absence of specimen, the conjugate saturates immobilized spike protein, marking the maximum signal output of the assay. However, neutralizing antibodies, if present in the specimen, will compete with invertase-ACE2 for binding to spike protein, reducing the signal output of the assay. Neutralizing antibodies that bind with extremely high affinity may outcompete ACE2 and evade detection by the Type I assay, but these antibodies will be detected using the Type II assay. Conversely, neutralizing antibodies that bind with low affinity may not effectively compete with ACE2 and will evade detection by the Type II assay, but these antibodies will be detected using the Type I assay. Binding kinetics of ACE2 and antibodies to immobilized spike protein and the competition kinetics between ACE2 and antibodies for spike protein binding will be measured using single-molecule microscopy.

Figure 10:
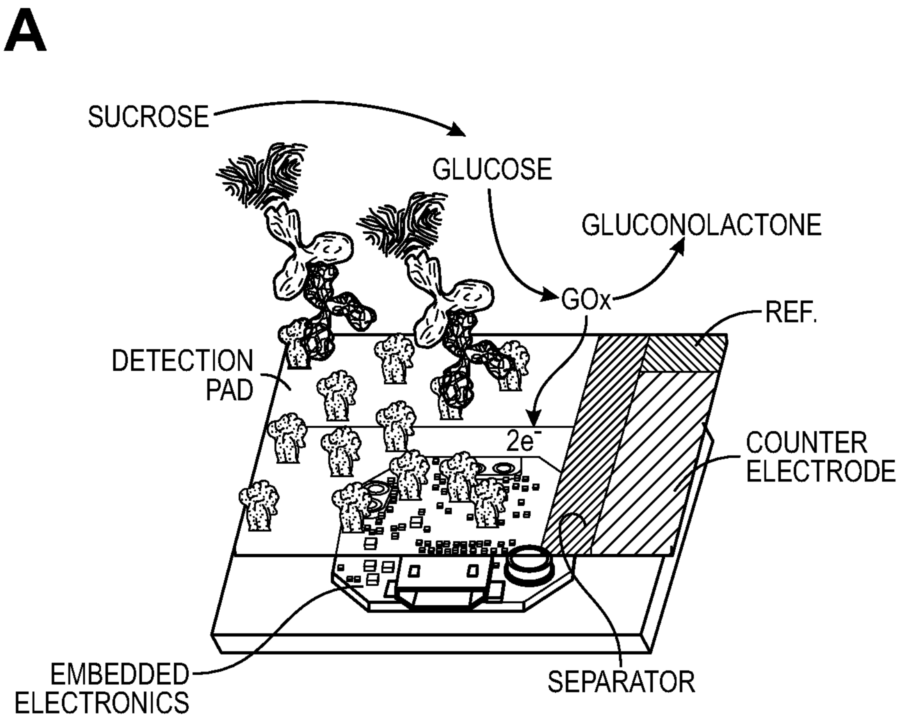
FIG. 10 (panels A and B) schematically show exemplary electrochemical detection schemes. (A) A fully integrated device can be produced in which cheap and disposable electronics embedded within the base of the device. (B) Alternatively, detection can also be achieved by directing the glucose produced in the sandwich immunoassay to a detection outlet (FIG. 2B) for measurement via a glucometer.
Figure 10:
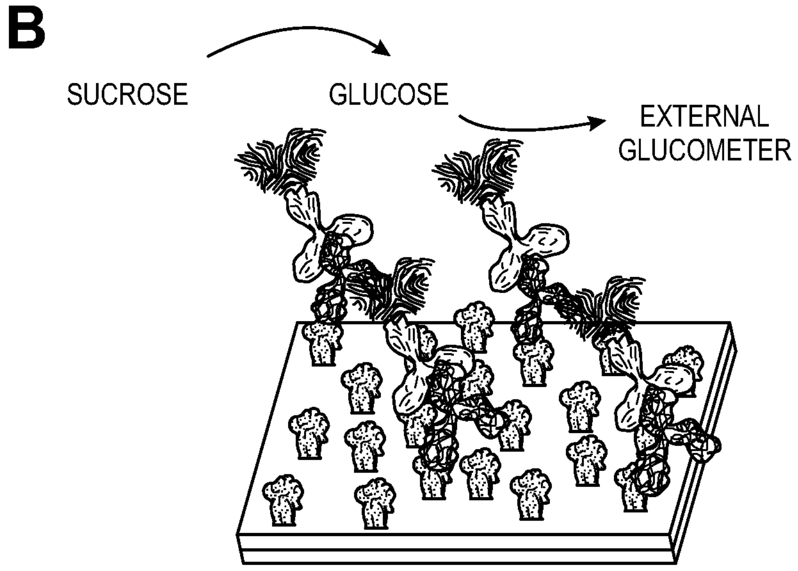

The assays can be performed on a self-driven microfluidic chip involving minimal user input (FIG. 1B). This integration is useful particularly when the antibody detection assay is implemented in non-laboratory settings. By performing this assay on the microscale, there is minimal reagent volume used (μL), and reactions occur fast to provide a rapid "sample-in-answer-out" response. The user workflow for device operation is also simple. A patient sample is first loaded into the appropriate inlet of the device containing pre-filled reagents in reservoirs. Following the introduction of the specimen, the device autonomously delivers reagents, in the correct order, over an assay pad (FIG. 3), glucose sensors (FIG. 10A), and out through the capillary pump. If a sample is positive for COVID-19 antibodies, then sucrose will be converted to glucose and an electrochemically generated readout can be made. An alternate readout methodology involves profiling glucose-containing solutions with a glucometer (FIG. 10B). The device does not need external pumps or pressure sources to function. Instead, fluid flow is driven by natural capillary pressure, which is dependent on fluid properties and channel geometries. To achieve this, capillaric components are integrated, which rely on modifying channel geometries for sequential reagent delivery in some embodiments.

Figure 8:
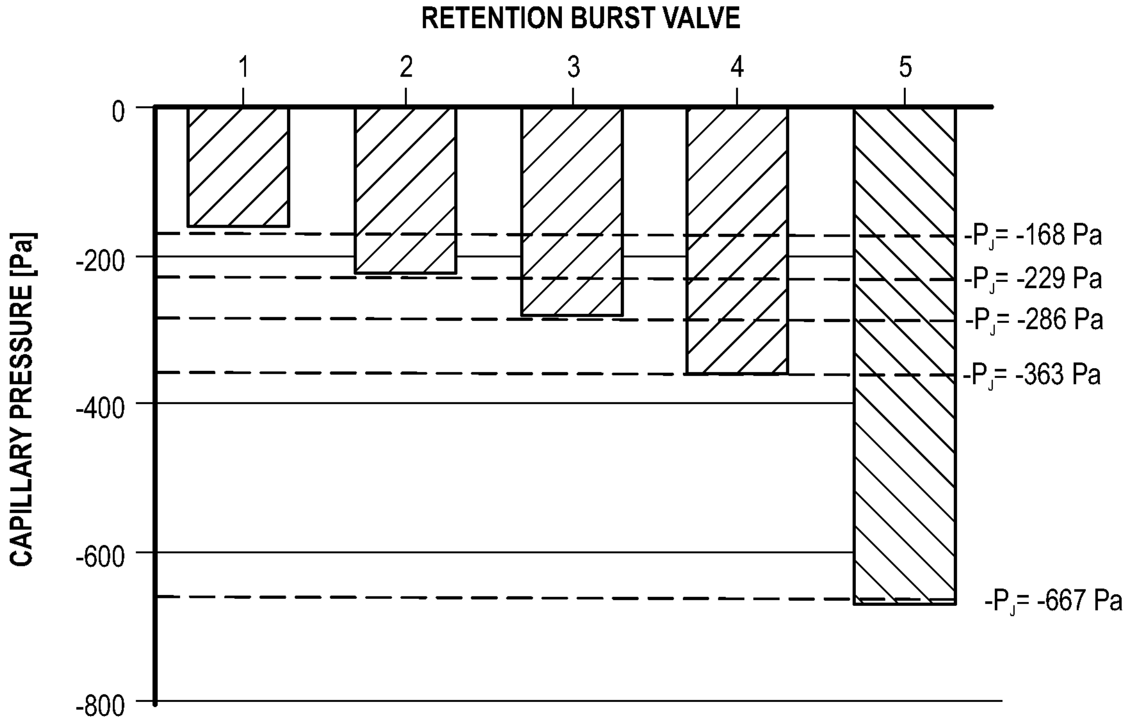
FIG. 8. Exemplary calculations of threshold pressures. The x-axis corresponds to each branch containing reagents. Dashed lines the junction pressure (universal for all branches) as branches get emptied. The sequence is down in order 1 to 4. The junction pressure bursting the branch 5, containing the sample, is designed to be the highest in order to eliminate unintentional bubble introduction into the main channel due to complete depletion of the sample.

In some embodiments, an initial step for developing a suitable microfluidic device is conducting theoretical calculations that ensure the proper delivery of reagents through the device. The device typically includes "branches" extending from a main microchannel (FIG. 2B). Each branch includes an inlet, retention burst valve (RBV), reservoir, and trigger valve (TV) in some embodiments. In some embodiments, the main microchannel leads to a serpentine fluidic resistor and a capillary pump (wide chamber filled with asymmetric pillars). The order of delivery is dictated by the capillary pressure created by the liquid air interface at the RBV, which can be modulated by channel dimensions and fluid properties. Initial calculations can be performed using surface tension and contact angles associated with, for example, the water/poly(methyl methacrylate) (PMMA) interface. By altering the dimensions of the fluidic resistor and capillary pump, the "junction pressure," the fluidic pressure at the entrance neck connecting the main channel and each reagent branch can be modified (FIG. 8). Once this junction pressure magnitude exceeds a threshold value, the RBV is triggered, and the fluid is emptied from the reagent branch, into the main channel and through the rest of the device. Channel geometries can be optimized such that sequential delivery of 5 unique reagents can be achieved in some embodiments. Downstream, a capillary pump that is large enough to prevent reagents from flowing out of the outlet to keep the assay self-contained is typically used.

Microfabrication protocols known to persons having ordinary skill in the art are typically use for the devices disclosed herein. In some embodiments, poly(methyl methacrylate) (PMMA) is used as the device substrate due to its high biocompatibility. PMMA sheets can be patterned with microscale features via hot embossing (FIG. 9), a process where PMMA sheets are pressed into a mold at high temperatures (>100° C.) and high forces (kN), using a benchtop press (Strongway, 10-Ton Hydraulic Shop Press, USA). Traditionally, PMMA sheets are molded with micromachined metal or cleanroom fabricated silicon molds, but these methods can be cumbersome and generally involve special facilities. Instead, in some embodiments, device molds are used with SLA 3D printing, a technique for fabrication of microfluidic devices with complex geometry. Compared to traditional cleanroom techniques, 3D printed fabrication typically allows rapid prototyping at a lower cost. A typical printer (Original Prusa SL1, Prusa Research, Czech Republic) has an XY resolution of 47 microns and a Z resolution of 10 microns. In some embodiments, a 3D printed mold is used to form an epoxy mold (Step 2 in FIG. 9B). In these embodiments, a positive mold is 3D printed and the part is sprayed with a silicone release spray. Subsequently, a high temperature, low viscosity epoxy can be poured on the mold, and the resin can be cured. Releasing the epoxy from the 3D printed mold yields the negative molds used for the hot embossing protocol. There may be challenges with releasing the epoxy mold from the 3D printed mold due to the stiffness of both materials. If so, a negative mold can be 3D printed and the silicone spray can be applied prior to pouring degassed poly(dimethylsiloxane) (PDMS) onto the mold. Following PDMS curing, this positive mold can be removed and used to form the negative high-temperature epoxy mold for hot embossing.

With the negative epoxy mold, the hot embossing protocol is used in certain embodiments. Features can be <1 mm tall, so ¼" (6.35 mm) PMMA sheets suffice as the substrate material in some embodiments. Using a hot embossing rig, the temperature, pressure, and hot embossing time are typically optimized to ensure that features are reliably transferred onto the PMMA sheet. In some embodiments, the features can be surface treated to further increase the hydrophilicity. This is optionally achieved by oxygen plasma treating the surface. While this is reliable for immediate usage, treated surfaces lose their hydrophilicity if not immediately wet. As such, other methods to maintain long-lived surface hydrophilicity for extended shelf-life are also optionally used. For example, stable hydrophilicity can be produced following oxygen plasma treatment with polyvinyl alcohol (PVA) and a second plasma treatment in some embodiments.

In some embodiments, an enclosed microfluidic device is formed by bonding the surface-treated PMMA features to a flat PMMA sheet, as can be done, for example, with solvents, plasma-treated poly(vinyl alcohol) (PVA), and thermal bonding. Any of these methods can be used or adapted for use as a bonding protocol for microfluidic device fabrication. In some embodiments, the performance of the complete microfluidic device relative to theoretical calculations is empirically determined using dyed water. The rate of individual reagent delivery is typically determined, as this frequently influences the incubation period for each reagent over the hydrogel substrate. In some embodiments, design iterations are used to optimize device performance and to resize device reservoirs to accommodate desired incubation periods.

During and/or after a given microfluidic device is produced, assay reagents are typically incorporated. The device should typically deliver reagents sequentially, so in some embodiment the branches are filled as follows: (1) wash buffer, (2) invertase anti-Ig, (3) wash buffer, (4) sucrose solution, and (5) patient specimen (FIG. 2B). In certain embodiments, dimensional adjustments can be made to address differences in contact angle and surface tension associated with wash buffer, sucrose, and patient samples. Similarly, the fluidic resistor dimensions can also be adjusted to account for hydrogel-attributed contact angle changes. The optimal protocol for a given hydrogel patterning on the PMMA sheet can be determined prior to device bonding. The hydrogel can be deposited anywhere downstream of the branches, including within the fluidic resistor in some embodiments. Bonding protocols can be further optimized, if needed, to maintain hydrogel integrity as the hydrogel is susceptible to solvent treatment and plasma exposure. Optionally, localized adhesive bonding methods are used instead of using complete surface treatments. For example, dilute epoxy resins are injected into the interstitial space between PMMA sheets with a needle in some embodiments.

Various methods of glucose detection are optionally used. In some embodiments, for example, the electrochemical detector is integrated within the disposable microfluidic device. To achieve this, an electronic circuit the size of a coin can be encased within the base of the device (FIG. 10A). This circuit can contain contact gold pins crossing the PMMA layer and touching the base of the assay pad. To achieve electrical conductivity across the gel, it can be doped with conducting nanowires. An adjacent but electrically separated pad can also be similarly prepared to create counter and reference electrodes. By keeping the hydrogel matrix as the electronic conductor and avoiding deposition of metals into the base plate, the complexity and number steps involved in detector preparation can be minimized. This configuration allows for continuous glucose readings.

In some embodiments, the assay pad is modified to not only contain spike protein but also glucose oxidase. In these embodiments, the current readout can be produced by the glucose oxidase-catalyzed oxidation of glucose via the cofactor flavin adenine dinucleotide (FAD/$FADH_2$), which is buried within the enzyme and facilitates efficient transfer of electrons to a redox mediator and then to a sensing electrode. The mediator, ([Os(4,4,-dimethylbipyridine)2]3+/2+), can be adapted from pre-existing glucose monitoring technology in some embodiments. The mediator and glucose oxidase enzyme can be covalently linked to a conductive polymer, poly(vinylimidazole), non-covalently bonded to the assay pad. To control the reference voltage of the system, an Ag/AgCl reference electrode in contact with the counter electrode can be used (FIG. 10A). This electrode can be prepared by doping the reference hydrogel with Ag/AgCl particles.

Alternatively, commercially available glucometers can be utilized to determine point glucose measurements (FIG. 1C & 10B). This can be achieved by modulating the capillary pump capacity and fluidic resistance, causing fluid to be deflected into the detection outlet (FIG. 2B) connected to an additional capillary pump to be activated only after saturation of the main pump in some embodiments. A manual way for a timed collection of the glucose containing assay end-product is also optionally used. During the first few minutes of operation, a wipe can cover the detection outlet to collect the various waste solutions. However, in the last assay step, the wipe can be removed to sample glucose containing solution via the glucometer to obtain desired readings in some of these embodiments.

Optionally, a microfluidic capillary device is constructed that creates deterministic outflowing streams of specimen and reagents directed towards multiple assay pads to achieve multiplexed parallel assays in some embodiments. In addition to the capillary flow-controlling parameters described herein, a varied channel geometry and capillaric elements can be used to construct stable bifurcating fluid networks. In this multi-channel device, the specimen injected into the main channel can be divided into daughter channels to perform simultaneous, parallelized detections of antibodies. The assay pads in these detections can be functionalized with full spike protein to evaluate the Type I and Type II assays, and controls, as described herein in some embodiments.

With a completed microfluidic device, assay conditions can be optimized (i.e., incubation times, reagent concentrations) to improve sample processing. If using an integrated glucose meter, for example, the output measurements can be calibrated with preset glucose samples, added between specimen addition and the first buffer wash. These calibration samples can be reported on sensor performance as a control for the final user.

Figure 11:
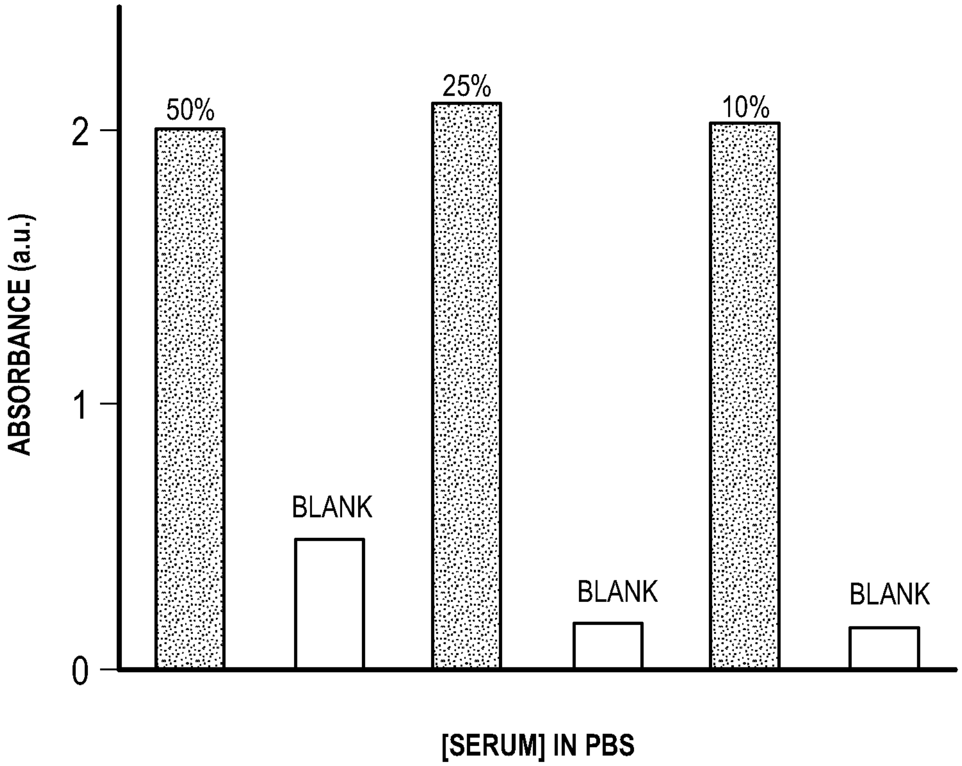
FIG. 11 is a plot of exemplary detection of SARS-CoV-2 antibodies in serum. These measurements were performed using the detection scheme presented in FIG. 4. In these, high signal-to-noise measurements of antibody levels comparable to those seen in COVID-19 patients in minimally diluted specimens was achieved.

In some embodiments, the antibody assays disclosed herein (FIG. 4) are validated by detecting antibodies in serum spiked with monoclonal antibodies. Although SARS-CoV-2 antibody levels are higher in serum relative to oral fluid, serum still represents a good proxy for the final matrix to be targeted. In serum, the platform is responding to normal antibody titers with good signal-to-noise ratios, at dilutions as low as 1:1 buffer-to-serum (FIG. 11). These assays are optimized for maximum signal output prior to testing in clinical specimens.

In some embodiments, a multiplexed device is used to achieve even splitting of specimen volumes when bifurcating into two individual assay channels, which contain neutralization assay pads as described herein. This provides an unparalleled platform for the point-of-need monitoring of immunity development following, for example, SARS-CoV-2 infection.

In some embodiments, the platform is validated according to the analytical sensitivity and specificity measures, as described below:

[1] Class specificity. The platform is able to discriminate between binding and neutralizing antibodies. In some embodiments, to validate the class specificity of the detection assay for neutralizing antibodies, three controls are employed. First, the assay is challenged with patient samples spiked with soluble ACE2 protein. Neutralizing antibodies in the sample compete with ACE2 for immobilized SARS-CoV-2 spike protein. Second, commercially available, high affinity human monoclonal neutralizing antibodies are used to demonstrate inhibition of ACE2 binding to immobilized spike protein. Third, pre-validated specimens are tested (e.g., banked SARS-CoV-2 specimens from the early stages of infection in the U.S., which were evaluated via virus neutralization assays to longitudinally determine neutralization against SARS-CoV-2). The diagnostic approaches disclosed herein compared against these reference samples can confirm the class specificity of the assays of the present disclosure.

[2] Cross-reactivity. In some embodiments, a lack of cross-reactivity for the platform is demonstrated using confirmed SARS-CoV-2 negative oral fluid specimens (N=125) obtained from various biobanks. The validation set can include additional oral fluid specimens ($N_{Total}$=120) with confirmed infections from a panel of 12 viruses (Table 1). The cross-reactivity can be assessed in specimens from patients with the underlying diseases in both the acute and convalescent stages.

TABLE 1

Clinical specimens for cross-reactivity evaluation

| Virus/Bacteria/Parasite antibody positive | N= |
|---|---|
| anti-influenza A (IgG and IgM) | 10 |
| anti-influenza B (IgG and IgM) | 10 |
| anti-HCV (IgG and IgM) | 10 |
| anti-HBV (IgG and IgM) | 10 |
| anti-Haemophilus influenza (IgG and IgM) | 10 |
| anti-229E (alpha coronavirus) | 10 |
| anti-NL63 (alpha coronavirus) | 10 |
| anti-OC43 (beta coronavirus) | 10 |
| anti-HKU1 (beta coronavirus) | 10 |
| ANA | 10 |
| anti-respiratory syncytial virus (IgG and IgM) | 10 |
| anti-HIV | 10 |
| confirmed SARS-CoV-2 | 125 |

[3] Clinical agreement study. In some embodiments, clinical agreement trials are performed using RT-PCR and optical immunoassays (e.g., Luminex) in oral fluid as the comparator methods to classify each specimen. In these embodiments, nasal swab specimens are typically used for RT-PCR and patient sera for immunoassay confirmations. The performance of the platform can be evaluated with prospective specimens. In some of these embodiments, clinical agreement (Table 2) is sought using SARS-CoV-2 positive specimens (N=125), aiming to achieve a minimum overall 90% positive percent agreement (PPA) and overall 95% negative percent agreement (NPA).

TABLE 2

Clinical agreement evaluation

| | | Comparator method | |
|---|---|---|---|
| | | Positive | Negative |
| Microfluidic platform | Positive | A | B |
| | Negative | C | D |

In some embodiments, the number of specimens needed is determined using a priori power analysis. In some of these embodiments, the analysis considers a t-test to evaluate the difference between two independent means (two groups) for each experiment. For the analysis, a two-tailed approach setting the probability error to $\alpha$=0.05, the power to $\beta$=0.95, and assuming an allocation ratio of 1 can be followed. The mean and variance values of Group 1 (RT-PCR/immunoassay) and Group 2 (electrochemical measurement) can be estimated based on literature values. This analysis resulted in an effect size of 0.32 and sample size N=125, as calculated via G*Power software version 3.1. N can be split into 62 males and 63 females (producing a sex-pooled N) to include any differences caused by these groups in the output of the antibody measurements. To determine PPA and NPA, (2×2) matrices (Table 2), and the relations: PPA=A/(A+C) & NPA=D/(B+D), where A=true positives, B=true negatives, C=false negatives, and D=false positives can be used.

In some embodiments, the collected sample volume can be adjusted by the modification of the swab size. In some embodiments, the selective surface attachment chemistry for spike protein onto the BSA gel is demonstrated, but additional substrate surface coatings are optionally used to further prevent non-specific binding of biomolecules in heavily loaded specimens. For example, to improve the performance of certain embodiments of the assay in undiluted samples, agents like casein and lysozyme can be incorporated. In some embodiments, invertase-based detection is used as described herein. Numerous other approaches for protein-protein and protein-surface conjugation are also optionally used (e.g., EDC-NHS coupling chemistry between amines and carboxylic acids, and other peptide coupling methods). Alternatively, other reactions based on maleimide-thiol, azide-alkyne click, and bromoalkylsilane-hydrazide-dicyclohexylcarbodiimide couplings are optionally used as needed to allow spike protein binding to arbitrary surfaces and protein-invertase conjugation. The microfluidic system is typically based on known fluidic control principles, such as capillarity. Washes between active solution deliveries can mitigate the risk of reagents mixing prematurely, and the numbers and volumes of wash solutions can be adjusted to minimize cross-contamination. The migration of produced glucose to the measurement outlet is robust, as the capillary pump is immediately behind the detector pad or measurement outlet, and the pump can be expanded if needed. The risk of nonspecific antibody binding to the trap region can also be minimized.

Figure 12:
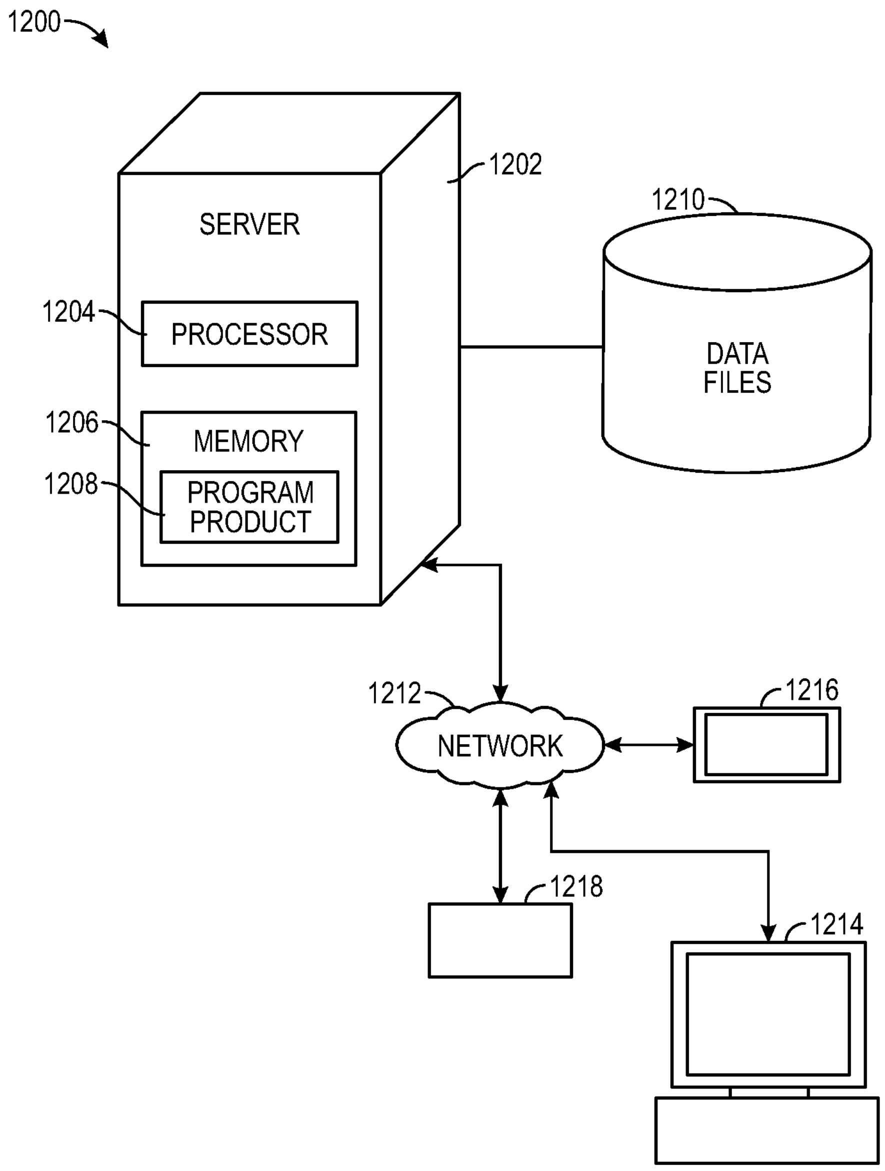
FIG. 12 is a schematic diagram of an exemplary system suitable for use with certain aspects disclosed herein.

The present disclosure also provides various systems and computer program products or machine-readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 12 provides a schematic diagram of an exemplary system suitable for use with implementing at least aspects of the methods disclosed in this application. As shown, system 1200 includes at least one controller or computer, e.g., server 1202 (e.g., a search engine server), which includes processor 1204 and memory, storage device, or memory component 1206, and one or more other communication devices 1214, 1216, (e.g., client-side computer terminals, telephones, tablets, laptops, other mobile devices, etc. (e.g., for receiving data for further analysis, etc.)) positioned remote from pathogen detection device 1218, and in communication with the remote server 1202, through electronic communication network 1212, such as the Internet or other internetwork. Communication devices 1214, 1216 typically include an electronic display (e.g., an internet enabled computer or the like) in communication with, e.g., server 1202 computer over network 1212 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 1200 also includes program product 1208 stored on a computer or machine readable medium, such as, for example, one or more of various types of memory, such as memory 1206 of server 1202, that is readable by the server 1202, to facilitate, for example, a guided search application or other executable by one or more other communication devices, such as 1214 (schematically shown as a desktop or personal computer). In some aspects, system 1200 optionally also includes at least one database server, such as, for example, server 1210 associated with an online website having data stored thereon (e.g., entries corresponding to more reference images, indexed therapies, etc.) searchable either directly or through search engine server 1202. System 1200 optionally also includes one or more other servers positioned remotely from server 1202, each of which are optionally associated with one or more database servers 1210 located remotely or located local to each of the other servers. The other servers can beneficially provide service to geographically remote users and enhance geographically distributed operations.

As understood by those of ordinary skill in the art, memory 1206 of the server 1202 optionally includes volatile and/or nonvolatile memory including, for example, RAM, ROM, and magnetic or optical disks, among others. It is also understood by those of ordinary skill in the art that although illustrated as a single server, the illustrated configuration of server 1202 is given only by way of example and that other types of servers or computers configured according to various other methodologies or architectures can also be used. Server 1202 shown schematically in FIG. 12, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 1200. As also understood by those of ordinary skill in the art, other user communication devices 1214, 1216 in these aspects, for example, can be a laptop, desktop, tablet, personal digital assistant (PDA), cell phone, server, or other types of computers. As known and understood by those of ordinary skill in the art, network 1212 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 1208 is optionally in the form of microcode, programs, cloud computing format, routines, and/or symbolic languages that provide one or more sets of ordered operations that control the functioning of the hardware and direct its operation. Program product 1208, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 1208 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 1208 is optionally copied from the computer-readable medium to a hard disk or a similar intermediate storage medium. When program product 1208, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes at least one result, data, and/or the like to be displayed or otherwise indicated (e.g., via a result indicator of device 1218 and/or via communication devices 1214, 1216 or the like) and/or receive information from other system components and/or from a system user (e.g., via communication devices 1214, 1216, or the like).

In some aspects, program product 1208 includes non-transitory computer-executable instructions which, when executed by electronic processor 1204 perform at least: detecting glucose and/or fructose, when the invertase converts sucrose to glucose and/or fructose.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of detecting a severe acute respiratory syndrome coronavirus-2 (SARS-COV-2) antibody in a sample, the method comprising:

contacting the sample with an epitope for binding the SARS-COV-2 antibody under conditions sufficient for the SARS-COV-2 antibody to bind the epitope to produce bound SARS-CoV-2 antibody;

contacting the bound antibody with one or more invertase-linked antibodies, or invertase-linked antigen binding portions thereof, that bind to the bound SARS-COV-2 antibody under conditions sufficient for the one or more invertase-linked antibodies, or the invertase-linked antigen binding portions thereof, to bind to the bound SARS-COV-2 antibody to produce a binding complex;

contacting the binding complex with one or more angiotensin-converting enzyme 2 (ACE2) receptors or with one or more invertase-ACE2 receptor conjugates;

contacting the binding complex with sucrose under conditions sufficient for the invertase to convert the sucrose to fructose and glucose; and, detecting the fructose and/or the glucose, thereby detecting the SARS-COV-2 antibody in the sample.

2. The method of claim 1, further comprising obtaining the sample from a test subject.

3. The method of claim 1, wherein the sample comprises an oral fluid sample obtained from a test subject.

* * * * *